US010082662B2

(12) United States Patent
Park et al.

(10) Patent No.: US 10,082,662 B2
(45) Date of Patent: Sep. 25, 2018

(54) 3D REFRACTIVE INDEX TOMOGRAPHY AND STRUCTURED ILLUMINATION MICROSCOPY SYSTEM USING WAVEFRONT SHAPER AND METHOD THEREOF

(71) Applicants: Korea Advanced Institute of Science and Technology, Daejeon (KR); Tomocube, Inc., Daejeon (KR)

(72) Inventors: YongKeun Park, Daejeon (KR); Seungwoo Shin, Daejeon (KR); Gwang Sik Park, Daejeon (KR)

(73) Assignees: KOREA ADVANCED INSTITUTE OF SCIENCE AND TECHNOLOGY, Daejeon (KR); TOMOCUBE, INC., Daejeon (KR)

( * ) Notice: Subject to any disclaimer, the term of this patent is extended or adjusted under 35 U.S.C. 154(b) by 81 days.

(21) Appl. No.: 15/243,265

(22) Filed: Aug. 22, 2016

(65) Prior Publication Data
US 2017/0357084 A1 Dec. 14, 2017

(30) Foreign Application Priority Data
Jun. 10, 2016 (KR) .......................... 10-2016-0072304

(51) Int. Cl.
*G02B 21/36* (2006.01)
*G01N 21/41* (2006.01)
(Continued)

(52) U.S. Cl.
CPC ....... *G02B 21/367* (2013.01); *G01N 21/4133* (2013.01); *G01N 21/45* (2013.01);
(Continued)

(58) Field of Classification Search
None
See application file for complete search history.

(56) References Cited

U.S. PATENT DOCUMENTS

2014/0347672 A1\* 11/2014 Pavillon ............... A61B 5/0066
356/491
2015/0177133 A1 6/2015 Choi et al.

FOREIGN PATENT DOCUMENTS

JP 05341195 A 12/1993
JP 2013524261 A 6/2013
(Continued)

OTHER PUBLICATIONS

Gustafsson "Surpassing the lateral resolution limit by a factor of two using structured illumination microscopy" Journal of Microscopy, vol. 198, Pt 2. May 2000 pp. 82-87.
(Continued)

*Primary Examiner* — Edwin Gunberg
(74) *Attorney, Agent, or Firm* — Hoffman Warnick LLC

(57) ABSTRACT

An ultra-high-speed 3D refractive index tomography and structured illumination microscopy system using a wavefront shaper and a method using the same are provided. A method of using an ultra-high-speed 3D refractive index tomography and structured illumination microscopy system that utilizes a wavefront shaper includes adjusting an irradiation angle of a plane wave incident on a sample by using the wavefront shaper, measuring a 2D optical field, which passes through the sample, based on the irradiation angle of the plane wave, and obtaining a 3D refractive index image from information of the measured 2D optical field by using an optical diffraction tomography or a filtered back projection algorithm.

12 Claims, 4 Drawing Sheets

(51) Int. Cl.
*G01N 21/64* (2006.01)
*G02B 21/16* (2006.01)
*G02B 26/08* (2006.01)
*G02B 27/46* (2006.01)
*G03H 1/00* (2006.01)
*G01N 21/45* (2006.01)
*G01N 21/17* (2006.01)

(52) U.S. Cl.
CPC ..... *G01N 21/6458* (2013.01); *G01N 21/6486* (2013.01); *G02B 21/16* (2013.01); *G02B 26/0833* (2013.01); *G02B 27/46* (2013.01); *G03H 1/0005* (2013.01); *G01N 2021/1787* (2013.01); *G01N 2201/0635* (2013.01); *G03H 2001/005* (2013.01)

(56) References Cited

FOREIGN PATENT DOCUMENTS

| JP | 2016511435 A | 4/2016 |
|---|---|---|
| WO | 2015109323 A2 | 7/2015 |
| WO | 2016004367 A1 | 1/2016 |

OTHER PUBLICATIONS

Gustafsson "Nonlinear structured-illumination microscopy: Widefield fluorescence imaging with theoretically unlimited resolution" PNAS vol. 102, No. 37, Sep. 13, 2005 pp. 13081-13086.

Lee "Binary computer-generated holograms" Applied Optics, vol. 18, No. 21, Nov. 1, 1979 pp. 3661-3669.

Shin "Active illumination using a digital micromirror device for quantitative phase imaging" Optic Letters, vol. 40, No. 22, Nov. 15, 2015 pp. 5407-5410.

Wolf "Three-dimensional structure determination of semi-transparent objects from holographic data" Optics Communications, vol. 1, No. 4, Aug. 11, 1969 pp. 153-156.

Shin et al., "Active illumination using a digital micromirror device for quantitive phase imaging," Optics Letters, vol. 40, No. 22, Nov. 15, 2015, 4 pages.

* cited by examiner

3D REFRACTIVE INDEX TOMOGRAPHY AND STRUCTURED ILLUMINATION MICROSCOPY SYSTEM USING WAVEFRONT SHAPER AND METHOD THEREOF

CROSS-REFERENCE TO RELATED APPLICATIONS

A claim for priority under 35 U.S.C. § 119 is made to Korean Patent Application No. 10-2016-0072304 filed Jun. 10, 2016, in the Korean Intellectual Property Office, the entire contents of which are hereby incorporated by reference.

BACKGROUND

Embodiments of the inventive concepts described herein relate to an ultra-high-speed 3-dimensional (3D) refractive index tomography and structured illumination microscopy system using a wavefront shaper and a method using the same, and more particularly, to a technology that simultaneously measures a 3D high resolution fluorescence image and a 3D refractive index stereoscopic image of a cell by using a single wavefront shaper.

Nowadays, methods used to optically measure an inner structure of a cell are a fluorescence image method that expresses a fluorescent protein in a specific structure of a cell and measures a fluorescence signal and a 3D refractive index tomography that measures a 3D refractive index distribution in the cell.

Without the label of the fluorescent protein, the 3D refractive index tomography is used which measures the reaction of a cell with respect to an incident wavefront and measures the 3D refractive index distribution in a cell. Since the measured refractive index value is linearly proportional to the concentration of protein being a major component in a cell, a biochemical property, such as the distribution of the concentration of protein, as well as a structural property in a cell may be obtained from the 3D refractive index distribution in the measured cell. In addition, since the label of a fluorescent protein is not used, the 3D refractive index tomography is noninvasively applied to a living cell. The 3D refractive index tomography may measure the reaction of a cell for a long time because photobleaching does not occur.

The 3D refractive index tomography using various kinds of wavefront shapers is provided to measure the 3D refractive index image of a cell (non-patent document 1). The 3D refractive index tomography makes a light from a coherent light source incident on a cell and measures a hologram of a transmitted light, which is diffracted from the cell, by using an interferometer.

In this case, the 3D refractive index tomography may measure a plurality of 2-dimensional (2D) holograms while an angle, at which a light enters the cell, is changed by using the wavefront shaper and may measure the 3D refractive index distribution of a cell by analyzing the measured hologram information through an algorithm.

Recently, it is possible to make the ultra-high-speed 3D optical diffraction tomography by using the digital micromirror device being a kind of wavefront shaper (non-patent document 2).

The optical diffraction tomography may obtain a protein distribution in a cell. However, it is difficult to distinguish a specific protein because the optical diffraction tomography is not a specific measure at the molecular level.

Furthermore, for the fluorescence image of a cell, a fluorescent protein is expressed in a specific organ (molecule) of the cell or dye is attached thereto. If an excitation light source enters the expressed fluorescence material, the fluorescent protein emits a fluorescence signal of another wavelength after absorbing the excitation light source. After the 3D optical diffraction tomography distinguishes an image of the inner structure of a cell through the fluorescence signal, it measures the distinguished image.

Recently, a structured illumination microscopy began to be applied to a method of increasing the resolution of a fluorescence image. The structured illumination microscopy is a method of obtaining an image of an ultra-high resolution, which exceeds the value of a diffraction limit by making an excitation light source incident on cell with a specific pattern and measuring a signal that is beyond an optically measurable range.

At first, after the structured illumination microscopy forms a pattern by allowing a light to pass through a diffraction lattice, it obtained an image by using the pattern (non-patent document 3). The structured illumination microscopy may measure an image by using various patterns while rotating and moving a lattice pattern and may obtain an image of a high resolution from an image of a low resolution through the algorithm. Afterward, the structured illumination microscopy may easily obtain the image of a high resolution through control of a pattern shape through the wavefront shaper.

Recently, a nonlinear structured illumination microscopy made it possible to improve the resolution (non-patent document 4). However, in the case of a fluorescence image, a process of dying a cell to express a fluorescent protein is invasive. If the fluorescence image is measured for a long time, the photobleaching occurs. In this case, it is impossible to measure the cell.

Non-Patent Documents

1. Wolf, E. (1969). "Three-dimensional structure determination of semi-transparent objects from holographic data." Optics Communications 1(4): 153-156.
2. Shin, S., et al. (2015). "Active illumination using a digital micromirror device for quantitative phase imaging." Optics letters 40(22): 5407-5410.
3. Gustafsson, M. G. (2000). "Surpassing the lateral resolution limit by a factor of two using structured illumination microscopy." Journal of microscopy 198(2): 82-87.
4. Gustafsson, M. G. (2005). "Nonlinear structured-illumination microscopy: wide-field fluorescence imaging with theoretically unlimited resolution." Proceedings of the National Academy of Sciences of the United States of America 102(37): 13081-13086.
5. Lee, W.-H. (1979). "Binary computer-generated holograms." Applied Optics 18(21): 3661-3669.

SUMMARY

Embodiments of the inventive concepts describe an ultra-high-speed 3D refractive index tomography and structured illumination microscopy system using a wavefront shaper and a method using the same and, in more detail, provide a technology that simultaneously measures a 3D high resolution fluorescence image and a 3D refractive index stereoscopic image of a cell by using a single wavefront shaper.

Embodiments of the inventive concepts provide an ultra-high-speed 3D refractive index tomography and structured illumination microscopy system using a wavefront shaper, which optically measures a 3D refractive index distribution in a living cell and a cellular tissue and simultaneously distinguishes a specific inner structure labeled by a fluorescent protein, and a method using the same.

One aspect of embodiments of the inventive concept is directed to provide a method of using an ultra-high-speed 3D refractive index tomography and structured illumination microscopy system that utilizes a wavefront shaper. The method includes adjusting an irradiation angle of a plane wave incident on a sample by using the wavefront shaper, measuring a 2D optical field, which passes through the sample, based on the irradiation angle of the plane wave, and obtaining a 3D refractive index image from information of the measured 2D optical field by using an optical diffraction tomography or a filtered back projection algorithm.

The method may further include adjusting a phase and a pattern of a wavefront of the plane wave to obtain a 3D high resolution fluorescence image. The 3D high resolution fluorescence image and the 3D refractive index image of the sample may be simultaneously measured by using the wavefront shaper.

The adjusting of the irradiation angle may include forming plane waves of various progression angles by changing a pattern displayed on a digital micromirror device, such that a progression angle of the plane wave incident on the sample is adjusted.

The adjusting of the irradiation angle may include adjusting a progression direction of one plane wave by adjusting the irradiation angle of the plane wave such that a diffraction light is incident on the sample and the rest thereof is shielded and adjusting a pattern of a digital micromirror device to obtain phase information.

The adjusting of the progression direction may include using only one of diffraction lights generated by the digital micromirror device by using a spatial filter.

The measuring of the 2D optical field may include creating an interference pattern between the 2D optical field, which passes through the sample, and a reference beam and measuring the 2D optical field while variously changing the irradiation angle of the plane wave.

The adjusting of the phase and the pattern may include making the plane wave incident on the sample with a pattern and adjusting a phase between plane waves of the pattern, obtaining a plurality of fluorescence images by using patterns controlled by adjusting the phase, and obtaining a 3D high resolution fluorescence image by reconstructing a 2D fluorescence image of a high resolution from the plurality of fluorescence images by using an algorithm.

The adjusting of the phase and the pattern may include forming 'N*M' patterns by using 'N' patterns for distinguishing an optical field, of which an angle and a phase are adjustable through a pattern of a digital micromirror device, and 'M' patterns for azimuthal angle scanning.

The method may further include selectively measuring a z-axis portion by using a low coherent light as a light source generating a plane wave after only the z-axis portion is distinguished.

The adjusting of the phase and the pattern may include obtaining the 3D high resolution fluorescence image by measuring each z-axis portion of the sample after translating a stage or a condenser lens in a z-axis direction.

Another aspect of embodiments of the inventive concept is directed to provide an ultra-high-speed 3D refractive index tomography and structured illumination microscopy system that utilizes a wavefront shaper. The system includes a modulation unit configured to adjust an irradiation angle of a plane wave incident on a sample by using the wavefront shaper, an interferometer configured to measure a 2D optical field, which passes through the sample, based on the irradiation angle of the plane wave, and a refractive index image unit configured to obtain a 3D refractive index image from information of the measured 2D optical field by using an optical diffraction tomography or a filtered back projection algorithm.

The system may further include a fluorescence image unit configured to adjust a phase and a pattern of a wavefront of the plane wave to obtain a 3D high resolution fluorescence image. The 3D high resolution fluorescence image and the 3D refractive index image of the sample may be simultaneously measured by using the wavefront shaper.

The modulation unit may adjust a progression direction of one plane wave by adjusting the irradiation angle of the plane wave such that a diffraction light is incident on the sample and the rest thereof is shielded, and may adjust a pattern of a digital micromirror device to obtain phase information.

The modulation unit may use only one of diffraction lights generated by the digital micromirror device by using a spatial filter.

The interferometer may create an interference pattern between the 2D optical field, which passes through the sample, and a reference beam and may measure the 2D optical field while variously changing the irradiation angle of the plane wave.

The fluorescence image unit may make the plane wave incident on the sample with a pattern, may obtain a plurality of fluorescence images by using patterns controlled by adjusting a phase between plane waves of the pattern, and may obtain a 3D high resolution fluorescence image by reconstructing a 2D fluorescence image of a high resolution from the plurality of fluorescence images by using an algorithm.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Hereinafter, embodiments of the inventive concept will be described with reference to accompanying drawings. However, embodiments to be described may be modified in the different forms, and the scope and spirit of the inventive concept is not limited by the embodiments to be described below. In addition, various embodiments are provided to describe this disclosure more fully to those skilled in the art. For a clear description, forms, sizes, and the like of elements may be exaggerated in a drawing.

To three-dimensionally analyze an inner structure of a cell and to measure the change in a structure in real time may be a technology that greatly contributes to the biological and pathological studies.

Embodiments to be described below provide a system and method that implements both a 3D refractive index tomography and a 3D structured illumination microscopy by using a wavefront shaper.

Embodiments may provide a technology that is capable of simultaneously measuring a 3D high resolution fluorescence image and a 3D refractive index stereoscopic image of a cell by using a single wavefront shaper and, in more detail, may provide an ultra-high-speed 3D refractive index tomography and structured illumination microscopy system using a wavefront shaper, which optically measures a 3D refractive index distribution in a living cell and a cellular tissue and simultaneously distinguishes a specific inner structure labeled by a fluorescent protein, and a method using the same.

Figure 1:
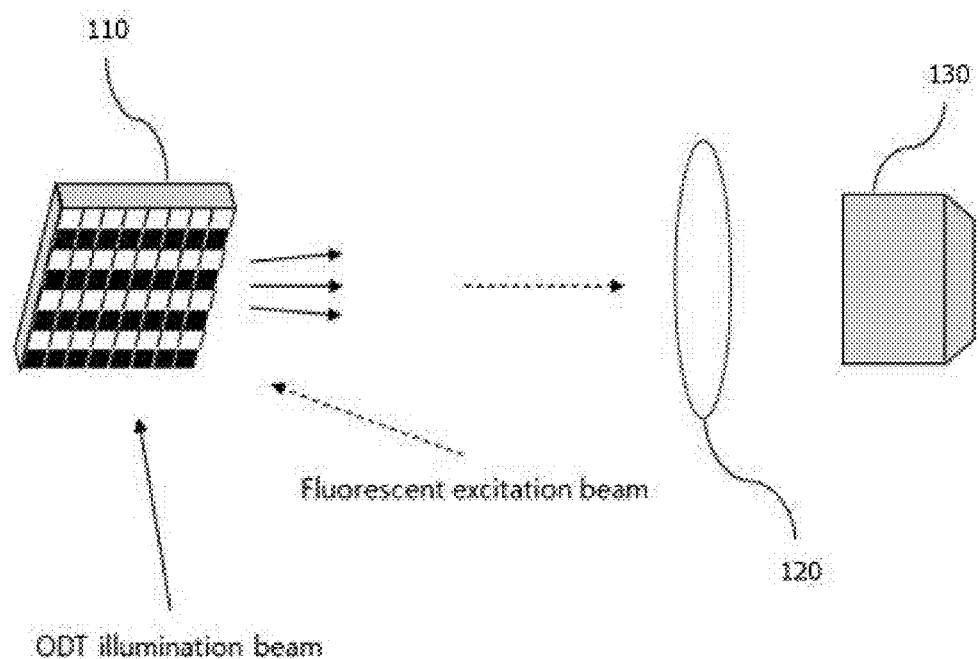
FIG. 1 is a drawing for describing an ultra-high-speed 3D refractive index tomography and structured illumination microscopy system by using a wavefront shaper, according to an embodiment.

FIG. 1 is a drawing for describing an ultra-high-speed 3D refractive index tomography and structured illumination microscopy system by using a wavefront shaper, according to an embodiment.

Referring to FIG. 1, one system that measures a 3D high resolution fluorescence image and a 3D refractive index distribution by using a wavefront shaper through a method of shaping an illuminated wavefront is illustrated.

To obtain a refractive index distribution in the 3D refractive index tomography, a sample image generated by plane waves of various angles is required. In addition, for a structured illumination microscopy, the phase and the pattern of an incident wavefront may be adjusted.

If the system uses the wavefront shaper, it may adjust the phase and the pattern of the wavefront of the plane wave as well as the incident angle of a plane wave. Accordingly, the system may obtain both the 3D high resolution fluorescence image and the 3D refractive index distribution image by using the wavefront shaper.

The ultra-high-speed 3D refractive index tomography and structured illumination microscopy system using the wavefront shaper according to an embodiment may include a modulation unit, an interferometer, a refractive index image unit, and a fluorescence image unit.

For example, the modulation unit may include a wavefront shaper 110, a tube lens 120, and a condenser lens 130. In addition, according to an embodiment, the modulation unit may further include a spatial filter.

The wavefront shaper 110 may be, for example, a digital micromirror device. That is, the digital micromirror device may be a wavefront shaper and may include an array having a plurality of micromirrors.

The tube lens 120 and the condenser lens 130 may make a plane wave incident on a sample by increasing the progression angle of the plane wave.

In this case, the sample may be an object to be measured, may be a cell, bacteria, a microbe, or the like, and may be a target including a cell or the like.

Furthermore, the interferometer may measure a 2D optical field, which passes through the sample, based on at least one or more of incident lights.

The refractive index image unit may obtain a 3D refractive index image from information of the measured 2D optical field.

The fluorescence image unit may adjust the phase and pattern of the wavefront of a plane wave to obtain the 3D high resolution fluorescence image.

Accordingly, the system may simultaneously measure the 3D high resolution fluorescence image and the 3D refractive index stereoscopic image of a sample by using the wavefront shaper.

Hereinafter, the ultra-high-speed 3D refractive index tomography and structured illumination microscopy system using the wavefront shaper will be described in detail.

First of all, to obtain a 3D refractive index tomogram, the system may adjust the irradiation angle of an incident plane wave by using the wavefront shaper through a Lee Hologram method (non-patent document 5). To adjust a progression angle of an incident plane wave, the system may properly change the Lee hologram pattern displayed on the digital micromirror device.

In more detail, to form plane waves of various progression angles by using the digital micromirror device, the Lee hologram pattern, which is expressed as Equation 1, may be input to the digital micromirror device.

$$f(x, y) = \frac{1}{2}[1 + \cos\{2\pi ux + 2\pi vy + \phi(x, y)\}] = \qquad \text{[Equation 1]}$$
$$\frac{1}{2} + \frac{1}{4}\exp[j2\pi(ux + vy)]\exp[j\phi(x, y)] +$$
$$\frac{1}{4}\exp[-j2\pi(ux + vy)]\exp[-j\phi(x, y)],$$

In this case, each of 'u' and 'v' may be a spatial frequency and may be a value that is adjusted through a pixel in the digital micromirror device. $\phi$ may denote the relative phase difference of a plane wave.

In the second equation in Equation 1, if the system makes only a diffraction light, which corresponds to the second of three terms, incident on a sample and shields the rest thereof, it may adjust the progression direction of one plane wave.

In the case where an optical axis is designated as z-axis and where angles of x-axis and y-axis directions of a laser plane wave having a specific wavelength $\lambda$ are respectively designated as $\theta_x$ and $\theta_y$, phase information of the wavefront corresponding thereto may be expressed as Equation 2.

$$\phi(x, y) = \frac{2\pi}{\lambda}\{x\sin\theta_x + y\sin\theta_y\} \qquad \text{[Equation 2]}$$

Accordingly, if the system adjusts the pattern of the digital micromirror device in Equation 1, it may obtain the desired phase information by using Equation 2. Here, to use one reflected light, the system may use only one of diffraction lights generated by the digital micromirror device through a spatial filter.

The system may create an interference pattern between the 2D optical field, which passes through the sample, and a reference beam, and may measure an optical field while variously changing the irradiation angle of the plane wave. The system may obtain the 3D refractive index image from information of the measured 2D optical field by using an optical diffraction tomography or a filtered back projection algorithm technology.

Next, to obtain the fluorescence image of the ultra-high resolution, the system may use the structured illumination microscopy.

To obtain an ultra-high resolution image in a structured illumination microscopy, the system may make the specific pattern incident on the sample and may adjust a phase between plane waves constituting the pattern.

For example, a sinusoidal pattern may be expressed as Equation 3.

$$f(x, y) = \frac{1}{2} + \frac{1}{4}\exp[j2\pi(ux + vy)]\exp[j\phi(x, y)] + \frac{1}{4}\exp[-j2\pi(ux + vy)]\exp[-j\phi(x, y)]$$ [Equation 3]

In this case, as described above, each of 'u' and 'v' may be a spatial frequency and may be a value that is adjusted through a pixel in the digital micromirror device. φ may denote the relative phase difference of the plane wave and may be adjusted through the pattern form of the digital micromirror device.

Figure 2:
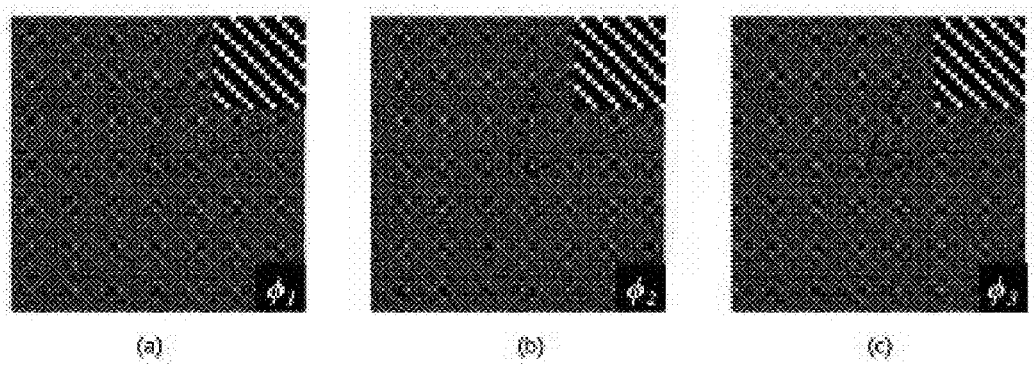
FIG. 2 is a drawing for describing a relative phase difference of a plane wave, according to an embodiment.

FIG. 2 is a drawing for describing a relative phase difference of a plane wave, according to an embodiment. Referring to FIG. 2, relative phase difference φ of a plane wave may be adjusted through a pattern form of a digital micromirror device.

In a 3D refractive index tomography, only the second of three terms in Equation 1 or 3 was used, but all the three terms may be used in a structured illumination microscopy.

In this case, a phase shifting method may be used to distinguish a time-based optical field on the three terms constituting the incident sinusoidal pattern and relative phase difference φ may be adjusted to another value that is greater than or equal to a value of three steps.

Figure 3:
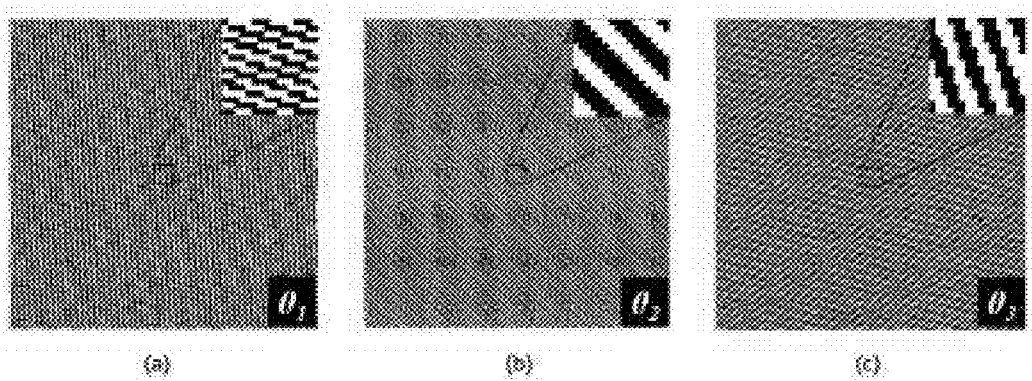
FIG. 3 is a drawing for describing adjusting of a spatial frequency, according to an embodiment.

Moreover, referring to FIG. 3, to maintain the azimuthal symmetry of a resolution, the system may measure various azimuthal angles θ by adjusting a spatial frequency while rotating the direction of the sinusoidal pattern.

That is, total 'N*M' patterns are needed due to 'N' patterns for distinguishing the optical field and 'M' patterns for azimuthal angle scanning. The angles and the phases of the patterns may be adjusted through the pattern of the digital micromirror device.

In this case, if the number of pixels of the digital micromirror is Λ, phase φ is adjusted to the step of $$\frac{2\pi}{\Lambda}.$$

Figure 4:
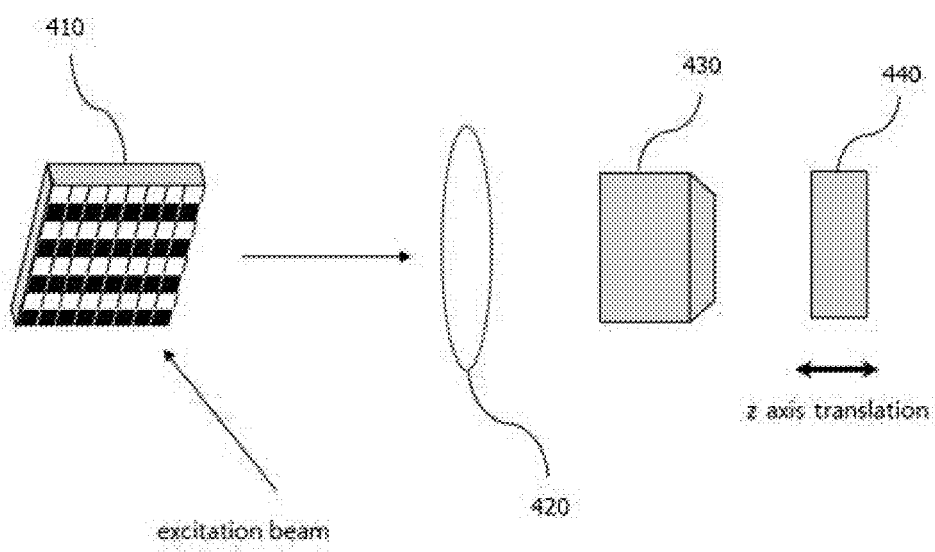
FIG. 4 is a drawing for describing a method of obtaining a 3D ultra-high resolution fluorescence image, according to an embodiment.

Referring to FIG. 4, the system may obtain fluorescence images by using the adjusted patterns and may reconstruct a 2D fluorescence image of an ultra-high resolution from the fluorescence images through an algorithm.

In addition, if the system uses a low coherent light as a light source, after it distinguishes only a specific z-axis portion, it may measure the distinguished portion. If the system measures each z-axis portion of a sample 440 after it translates a stage or a condenser lens 430 in the z-axis direction, it may obtain the 3D ultra-high resolution fluorescence image. Meanwhile, as described in FIG. 1, the modulation unit may include a wavefront shaper 410, a tube lens 420, and the condenser lens 430. In addition, according to an embodiment, the modulation unit may further include a spatial filter.

Hereinafter, a system and a method that obtain the 3D refractive index tomography image and the 3D high resolution fluorescence image will be described in detail.

Figure 5:
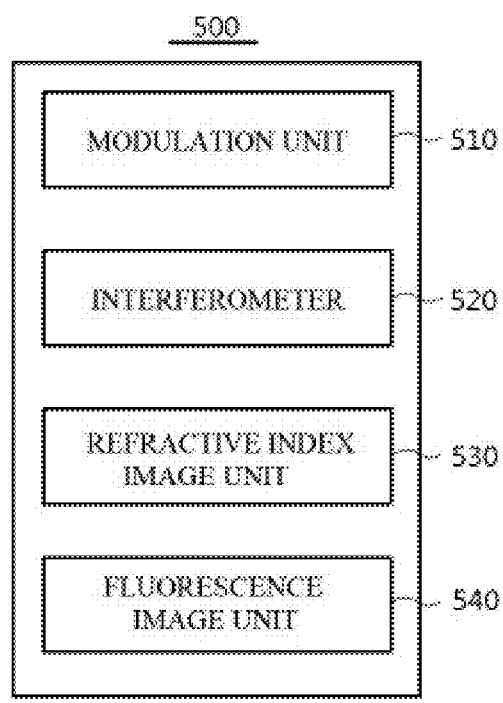
FIG. 5 is a block diagram illustrating an ultra-high-speed 3D refractive index tomography and structured illumination microscopy system that uses a wavefront shaper, according to an embodiment.

FIG. 5 is a block diagram illustrating an ultra-high-speed 3D refractive index tomography and structured illumination microscopy system that uses a wavefront shaper, according to an embodiment.

Referring to FIG. 5, according to an embodiment, an ultra-high-speed 3D refractive index tomography and structured illumination microscopy system 500 using the wavefront shaper may include a modulation unit 510, an interferometer 520, and the refractive index image unit 530. According to an embodiment, the ultra-high-speed 3D refractive index tomography and structured illumination microscopy system 500 using the wavefront shaper may further include a fluorescence image unit 540.

The modulation unit 510 may adjust the irradiation angle of a plane wave incident on a sample by using the wavefront shaper.

In more detail, the modulation unit 510 may make a light incident on a sample by changing at least one or more of the irradiation angle and the wavefront pattern of an incident light by using the wavefront shaper. In this case, the wavefront shaper may use a device, which is capable of adjusting the phase of the light, or a film, in which the phase is capable of being adjusted, in the fixed form. For example, the wavefront shaper may include a digital micromirror device that is capable of adjusting a wavefront at a high speed. The digital micromirror device may be a wavefront shaper and may include an array having a plurality of micromirrors.

That is, to adjust a progression angle of a plane wave incident on a sample, the modulation unit 510 may form the plane waves of various progression angles by changing a pattern displayed on the digital micromirror device.

In addition, the modulation unit 510 may adjust the progression direction of one plane wave by adjusting the irradiation angle of a plane wave such that a diffraction light is incident on a sample and the rest thereof is shield and may adjust the pattern of the digital micromirror device to obtain the specific phase information.

In this case, the modulation unit 510 may use only specific one of diffraction lights, which is generated by the digital micromirror device, by using a spatial filter.

Meanwhile, after the modulation unit 510 distinguishes only a specific z-axis portion, it may measure the distinguished z-axis portion by using a low coherent light as a light source that generates a plane wave.

For example, the modulation unit 510 may include a digital micromirror device, a tube lens, and a condenser lens. In addition, according to an embodiment, the modulation unit 510 may further include a spatial filter.

The interferometer 520 may extract an interference signal from at least one or more incident lights and may measure a 2D optical field, which passes through a sample, based on the at least one or more incident lights.

That is, the interferometer 520 may measure the 2D optical field that passes through the sample according to the irradiation angle of the plane wave.

The interferometer 520 may create an interference pattern between the 2D optical field, which passes through the sample, and a reference beam and may measure the 2D optical field while variously changing the irradiation angle of the plane wave.

The refractive index image unit 530 may precisely measure a 3D refractive index at a high speed by obtaining a 3D refractive index image through information of the measured 2D optical field.

In more detail, the refractive index image unit 530 may obtain the 3D refractive index image from the information of the measured 2D optical field by using an optical diffraction tomography or a filtered back projection algorithm technology.

The fluorescence image unit 540 may adjust the phase and pattern of the wavefront of a plane wave to obtain the 3D high resolution fluorescence image. Accordingly, the fluorescence image unit 540 may simultaneously measure the 3D high resolution fluorescence image and the 3D refractive index stereoscopic image of a sample by using the wavefront shaper.

In more detail, the fluorescence image unit 540 may make a plane wave incident on a sample with a specific pattern, may obtain a fluorescence image by using patterns controlled by adjusting a phase between plane waves constituting the pattern, and may obtain a 3D high resolution fluorescence image by reconstructing a 2D fluorescence image of a high resolution from a plurality of fluorescence images by using an algorithm.

The fluorescence image unit 540 may form 'N*M' patterns by using 'N' patterns for distinguishing an optical field, of which an angle and a phase are adjustable, through the pattern of a digital micromirror device and 'M' patterns for azimuthal angle scanning.

The fluorescence image unit 540 may obtain the 3D ultra-high resolution fluorescence image by measuring each z-axis portion of a sample after translating a stage or a condenser lens in the z-axis direction.

According to an embodiment, an ultra-high-speed 3D refractive index tomography and structured illumination microscopy system using a wavefront shaper, which optically measures a 3D refractive index distribution in a living cell and a cellular tissue and simultaneously distinguishes a specific inner structure labeled by a fluorescent protein, and a method using the same may be provided.

Figure 6:
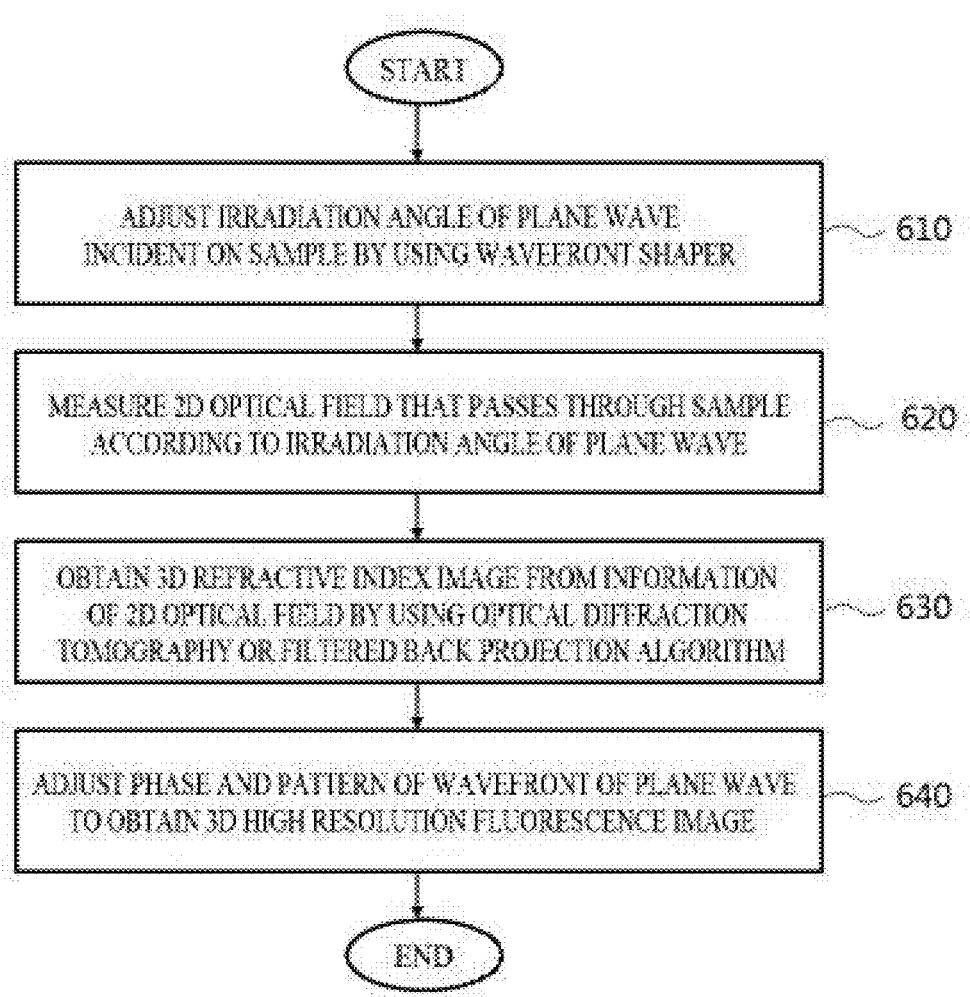
FIG. 6 is a flowchart illustrating a method of using an ultra-high-speed 3D refractive index tomography and structured illumination microscopy system that uses a wavefront shaper, according to an embodiment.

FIG. 6 is a flowchart illustrating a method of using an ultra-high-speed 3D refractive index tomography and structured illumination microscopy system that uses a wavefront shaper, according to an embodiment.

According to an embodiment, a method of using an ultra-high-speed 3D refractive index tomography and structured illumination microscopy system that utilizes a wavefront shaper includes step 610 of adjusting an irradiation angle of a plane wave incident on a sample by using the wavefront shaper, step 620 of measuring a 2D optical field, which passes through the sample, based on the irradiation angle of the plane wave, and step 630 of obtaining a 3D refractive index image from information of the measured 2D optical field by using an optical diffraction tomography or a filtered back projection algorithm.

Furthermore, the method may further include step 640 of the adjusting of the phase and the pattern of a wavefront of a plane wave to obtain a 3D high resolution fluorescence image.

Accordingly, the system may simultaneously measure the 3D high resolution fluorescence image and the 3D refractive index stereoscopic image of a sample by using the wavefront shaper.

Hereinafter, according to an embodiment, a method of using an ultra-high-speed 3D refractive index tomogram and fluorescence structured illumination microscopy system by using a wavefront shaper will be described in detail as an example.

The method of using an ultra-high-speed 3D refractive index tomogram and fluorescence structured illumination microscopy system by using a wavefront shaper will be described in detail by using the method of using an ultra-high-speed 3D refractive index tomogram and fluorescence structured illumination microscopy system by using a wavefront shaper that is described in FIG. 5.

According to an embodiment, the high-speed 3D refractive index tomogram and fluorescence structured illumination microscopy system 500 using a wavefront shaper may include the modulation unit 510, the interferometer 520, and the refractive index image unit 530. According to an embodiment, the ultra-high-speed 3D refractive index tomography and structured illumination microscopy system 500 using the wavefront shaper may further include the fluorescence image unit 540.

In step 610, the modulation unit 510 may adjust an irradiation angle of a plane wave incident on a sample by using a wavefront shaper.

For example, the wavefront shaper may use a digital micromirror device, or the like. That is, to adjust the progression angle of a plane wave incident on a sample, the modulation unit 510 may form the plane waves of various progression angles by changing a pattern displayed on the digital micromirror device.

In addition, the modulation unit 510 may adjust the progression direction of one plane wave by adjusting the irradiation angle of a plane wave such that a diffraction light is incident on a sample and the rest thereof is shield and may adjust the pattern of the digital micromirror device to obtain the specific phase information.

In this case, the modulation unit 510 may use only specific one of diffraction lights, which is generated by the digital micromirror device, by using a spatial filter.

In step 620, the interferometer 520 may measure the 2D optical field that passes through the sample according to the irradiation angle of the plane wave.

In more detail, the interferometer 520 may create an interference pattern between the 2D optical field, which passes through the sample, and a reference beam and may measure the 2D optical field while variously changing the irradiation angle of the plane wave.

In step 630, the refractive index image unit 530 may obtain the 3D refractive index image from the information of the measured 2D optical field by using an optical diffraction tomography or a filtered back projection algorithm technology.

In step 640, the fluorescence image unit 540 may adjust the phase and pattern of the wavefront of a plane wave to obtain the 3D high resolution fluorescence image. Accordingly, the fluorescence image unit 540 may simultaneously measure the 3D high resolution fluorescence image and the 3D refractive index stereoscopic image of a sample by using the wavefront shaper.

In more detail, the fluorescence image unit 540 may make a plane wave incident on a sample with a specific pattern, may obtain a fluorescence image by using patterns controlled by adjusting a phase between plane waves constituting the pattern, and may obtain a 3D high resolution fluorescence image by reconstructing a 2D fluorescence image of a high resolution from a plurality of fluorescence images by using an algorithm.

The fluorescence image unit 540 may form 'N*M' patterns by using 'N' patterns for distinguishing an optical field, of which an angle and a phase are adjustable, through the pattern of a digital micromirror device and 'M' patterns for azimuthal angle scanning.

Meanwhile, after the modulation unit 510 distinguishes only a specific z-axis portion, it may measure the distinguished z-axis portion by using a low coherent light as a light source that generates a plane wave.

In other words, the fluorescence image unit 540 may obtain a 3D fluorescence image through optical sectioning by using a z-axis shift stage and a low coherent light that is patterned by using a diffraction lattice or a digital micromirror device being a type of wavefront shaper.

The fluorescence image unit 540 may obtain the 3D ultra-high resolution fluorescence image by measuring each z-axis portion of a sample after translating a stage or a condenser lens in the z-axis direction.

According to an embodiment, one system may measure both a 3D ultra-high resolution fluorescence image and a 3D refractive index distribution image of a living cell. After the system distinguishes a specific structure labelled through a 3D protein distribution in a cell and the 3D ultra-high resolution fluorescence image, it may measure the specific structure by using the technique.

In addition, structural and biochemical changes may also be measured according to a time by measuring the inner structure of a cell for a long time. The technology provided from the inventive concept may greatly contribute to the biological and pathological studies at the cellular level.

While a few exemplary embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned elements, such as systems, structures, devices, or circuits, are combined or coupled in different forms and modes than as described above or be substituted or switched with other components or equivalents.

According to an embodiment, an ultra-high-speed 3D refractive index tomography and structured illumination microscopy system using a wavefront shaper, which simultaneously measures a 3D high resolution fluorescence image and a 3D refractive index stereoscopic image of a cell as a single wavefront shaper, and a method using the same may be provided.

According to an embodiment, an ultra-high-speed 3D refractive index tomography and structured illumination microscopy system using a wavefront shaper, which optically measures a 3D refractive index distribution in a living cell and a cellular tissue and simultaneously distinguishes a specific inner structure labeled by a fluorescent protein, and a method using the same may be provided.

Therefore, other implements, other embodiments, and equivalents to claims are within the scope of the following claims.

What is claimed is:

1. A method of using an ultra-high-speed 3-dimensional (3D) refractive index tomography and structured illumination microscopy system that utilizes a wavefront shaper, the method comprising:
adjusting an irradiation angle of a plane wave incident on a sample by using the wavefront shaper;
measuring a 2-dimensional (2D) optical field, which passes through the sample, based on the irradiation angle of the plane wave; and
obtaining a 3D refractive index image from information of the measured 2D optical field by using an optical diffraction tomography or a filtered back projection algorithm,
wherein the adjusting of the irradiation angle comprises:
adjusting a progression direction of one plane wave by adjusting the irradiation angle of the plane wave such that a diffraction light is incident on the sample and the rest thereof is shielded; and
adjusting a pattern of a digital micromirror device to obtain phase information.

2. The method of claim 1, further comprising:
adjusting a phase and a pattern of a wavefront of the plane wave.

3. The method of claim 1, wherein the adjusting of the progression direction comprises:
using only one of diffraction lights generated by the digital micromirror device by using a spatial filter.

4. The method of claim 1, wherein the measuring of the 2D optical field comprises:
creating an interference pattern between the 2D optical field, which passes through the sample, and a reference beam and measuring the 2D optical field while variously changing the irradiation angle of the plane wave.

5. The method of claim 2, wherein the adjusting of the phase and the pattern comprises:
making the plane wave incident on the sample with a pattern and adjusting a phase between plane waves of the pattern;
obtaining a plurality of fluorescence images by using patterns controlled by adjusting the phase; and
obtaining a 3D high resolution fluorescence image by reconstructing a 2D fluorescence image of a high resolution from the plurality of fluorescence images by using an algorithm.

6. The method of claim 2, wherein the adjusting of the phase and the pattern comprises:
forming 'N*M' patterns by using 'N' patterns for distinguishing an optical field, of which an angle and a phase are adjustable through a pattern of a digital micromirror device, and 'M' patterns for azimuthal angle scanning.

7. The method of claim 2, wherein the adjusting of the phase and the pattern comprises:
obtaining the 3D high resolution fluorescence image by measuring each z-axis portion of the sample after translating a stage or a condenser lens in a z-axis direction.

8. An ultra-high-speed 3D refractive index tomography and structured illumination microscopy system that utilizes a wavefront shaper, the system comprising:
a modulation unit configured to adjust an irradiation angle of a plane wave incident on a sample by using the wavefront shaper;
an interferometer configured to measure a 2D optical field, which passes through the sample, based on the irradiation angle of the plane wave; and
a refractive index image unit configured to obtain a 3D refractive index image from information of the measured 2D optical field by using an optical diffraction tomography or a filtered back projection algorithm,
wherein the modulation unit adjusts a progression direction of one plane wave by adjusting the irradiation angle of the plane wave such that a diffraction light is incident on the sample and the rest thereof is shielded, and adjusts a pattern of a digital micromirror device to obtain phase information.

9. The system of claim 8, further comprising:
a fluorescence image unit configured to adjust a phase and a pattern of a wavefront of the plane wave.

10. The system of claim 8, wherein the modulation unit uses only one of diffraction lights generated by the digital micromirror device by using a spatial filter.

11. The system of claim 8, wherein the interferometer creates an interference pattern between the 2D optical field, which passes through the sample, and a reference beam and measures the 2D optical field while variously changing the irradiation angle of the plane wave.

12. The system of claim 9, wherein the fluorescence image unit makes the plane wave incident on the sample with a pattern, obtains a plurality of fluorescence images by using patterns controlled by adjusting a phase between plane waves of the pattern, and obtains a 3D high resolution fluorescence image by reconstructing a 2D fluorescence image of a high resolution from the plurality of fluorescence images by using an algorithm.

* * * * *